United States Patent
Van Horn et al.

(10) Patent No.: US 11,931,333 B1
(45) Date of Patent: Mar. 19, 2024

(54) TOPICAL TREATMENT OF HERPES INFECTIONS

(71) Applicants: Peter Van Horn, Salt Lake City, UT (US); John M. Guynn, Salt Lake City, UT (US)

(72) Inventors: Peter Van Horn, Salt Lake City, UT (US); John M. Guynn, Salt Lake City, UT (US)

( * ) Notice: Subject to any disclaimer, the term of this patent is extended or adjusted under 35 U.S.C. 154(b) by 351 days.

(21) Appl. No.: 16/886,730

(22) Filed: May 28, 2020

Related U.S. Application Data

(60) Provisional application No. 62/853,712, filed on May 28, 2019.

(51) Int. Cl.
| | |
|---|---|
| *A61K 31/352* | (2006.01) |
| *A61K 9/00* | (2006.01) |
| *A61K 9/06* | (2006.01) |
| *A61K 9/107* | (2006.01) |
| *A61K 31/05* | (2006.01) |
| *A61K 31/522* | (2006.01) |
| *A61K 47/10* | (2017.01) |
| *A61K 47/14* | (2017.01) |
| *A61K 47/18* | (2017.01) |
| *A61K 47/20* | (2006.01) |
| *A61K 47/44* | (2017.01) |
| *A61P 31/22* | (2006.01) |

(52) U.S. Cl.
CPC ............ *A61K 31/352* (2013.01); *A61K 31/05* (2013.01); *A61K 31/522* (2013.01); *A61K 47/10* (2013.01); *A61K 47/14* (2013.01); *A61K 47/183* (2013.01); *A61K 47/20* (2013.01); *A61K 47/44* (2013.01); *A61P 31/22* (2018.01); *A61K 9/0014* (2013.01); *A61K 9/0053* (2013.01); *A61K 9/06* (2013.01); *A61K 9/107* (2013.01)

(58) Field of Classification Search
CPC ...... A61K 31/522; A61K 47/10; A61K 47/14; A61K 47/20; A61P 31/22
See application file for complete search history.

(56) References Cited

U.S. PATENT DOCUMENTS

| | | | | |
|---|---|---|---|---|
| 4,499,084 | A * | 2/1985 | Dixon | C07H 19/16 536/27.23 |
| 4,935,448 | A * | 6/1990 | Baldone | A61K 31/445 514/642 |
| 6,946,490 | B2 | 9/2005 | Squires | |
| 8,470,769 | B2 * | 6/2013 | O'Neil | A61P 31/10 514/2.7 |
| 2010/0273895 | A1 * | 10/2010 | Stinchcomb | A61P 17/14 514/733 |

OTHER PUBLICATIONS

Capriotti, Kara, et al., "Dimethyl Sulfoxide History, Chemistry, and Clinical Utility in Dermatology", Literature Review, The Journal of Clinical and Aesthetic Dermatology, Sep. 2012, vol. 5, No. 9.
Puvion-Dutilleul F, et al., "Effect of dehydrating agents of DNA organization in herpes viruses", J. Histochem Cytochem 1987 (Jun; 35(6): 635-45.
JS Aguilar, et al., "Dimethyl sulfoxide blocks herpes simplex virus-1 productive infection in vitro acting at different stages with positive cooperativity. Application of micro-array analysis", BioMed Central, BMC Infectious Diseases, May 24, 2002.
Fast Results Genital Herpes Treatment, Medically reviewed by Drugs.com. Last updated on May 12, 2020, https://www.drugs.com/otc/115864/fast-results-genital-herpes-treatment.html.
MPR the Right Does of Information, Fast-Results! Available soon for genital herpes symptom relief, Mar. 23, 2010, https://www.empr.com/home/news/fast-results-available-soon-for-genital-herpes-symptom-relief/.
Michael Johnsen, Drug Store News, "Merix unveils new over-the-counter genital herpes treatment" Mar. 12, 2010; https://www.drugstorenews.com/otc/merix-unveils-new-over-counter-genital-herpes-treatment/.

* cited by examiner

*Primary Examiner* — Sahar Javanmard
(74) *Attorney, Agent, or Firm* — Workman Nydegger

(57) ABSTRACT

A topical composition for treating genital herpes includes dimethyl sulfoxide (DMSO), a diluent, and a quaternary ammonium compound. The topical composition may further contain a cannabinoid component, such as CBD, and/or a terpene and/or an essential oil. The topical composition may be in the form of a two-component composition in which a first topical composition includes dimethyl sulfoxide (DMSO), a diluent, and a quaternary ammonium compound and the second topical composition includes dimethyl sulfoxide (DMSO), a diluent, and a cannabinoid component.

19 Claims, No Drawings

TOPICAL TREATMENT OF HERPES INFECTIONS

CROSS REFERENCE TO RELATED APPLICATION

This application claims the benefit of U.S. Provisional Patent Application No. 62/853,712, filed May 28, 2019, which is incorporated by reference in its entirety.

BACKGROUND OF THE INVENTION

1. Field of the Invention

The invention is in the field of topical formulations for treating herpes infections, such as genital herpes, oral herpes, and shingles.

2. Relevant Technology

Genital herpes is a sexually transmitted disease caused by herpes simplex 2 virus (HSV-2). Many can be infected yet have no or mild symptoms and not know they are infected. When symptoms do occur, they typically include small blisters that break open to form painful ulcers. Flu-like symptoms, such as fever, aching, or swollen lymph nodes, may also occur. Onset is typically around 4 days after exposure, with symptoms lasting up to 4 weeks. Once infected, further outbreaks may occur but are generally milder.

The disease is typically spread by direct genital contact with the skin surface or secretions of someone who is infected. This may occur during sex, including vaginal, anal, and oral sex. Sores are not required for transmission to occur. The risk of spread between a couple is about 7.5% over a year. HSV is classified into two types, HSV-1 and HSV-2. While historically most genital herpes infections are caused by HSV-2, genital HSV-1 has become more common in the developed world. HSV-1 is usually associated with oral herpes (e.g., cold sores).

Efforts to prevent infection include abstaining from sex, using condoms, and only having sex with someone not infected. Once infected, there is no known cure. Antiviral drugs can prevent, reduce, or shorten outbreaks when they occur. Long-term use of antivirals may decrease the risk of further spread.

In 2015, about 846 million people (12% of the world population) had genital herpes. In the United States, more than one in six people has HSV-2. Women are more commonly infected than men. Complications may include aseptic meningitis, increased risk of HIV/AIDS if exposed to HIV-positive individuals, and spread to a baby during childbirth, resulting in neonatal herpes.

In males, lesions usually occur on the glans penis, shaft of the penis, other parts of the genital region, inner thigh, buttocks, and/or anus. In females, lesions can appear on or near the vulva, clitoris, labia, buttocks, and/or anus.

Common symptoms include pain, itching, and burning. Less frequent yet still common symptoms include discharge from the penis or vagina, fever, headache, muscle pain (myalgia), swollen and enlarged lymph nodes, and malaise. Women often experience additional symptoms such as painful urination (dysuria) and cervicitis. Herpetic proctitis (inflammation of the anus and rectum) is common for individuals participating in anal intercourse.

After a first episode of herpes genitalis caused by HSV-2, there will be at least one recurrence in approximately 80% of people, while the recurrence rate for herpes genitalis caused by HSV-1 is approximately 50%. Herpes genitalis caused by HSV-2 recurs on average four to six times per year, while that of HSV-1 infection occurs only about once per year.

Antiviral medications, such as acyclovir, valacyclovir, famciclovir, and penciclovir, may prevent herpes outbreaks or shorten outbreaks if they occur.

Acyclovir is an antiviral medication and reduces the pain and the number of lesions in the initial case of genital herpes. Furthermore, it decreases the frequency and severity of recurrent infections. It comes in capsules, tablets, suspension, injection, powder for injection, and ointment. The ointment is used topically and decreases pain, reduces healing time, and limits the spread of the infection.

Valacyclovir is a prodrug that is converted to acyclovir once in the body. It helps relieve the pain and discomfort and speeds healing of sores. It only comes in caplets and has a longer duration of action than acyclovir. An example usage is by mouth twice per day for ten days for primary lesions, and twice per day for three days for a recurrent episode.

Famciclovir is another antiviral drug that belongs to the same class. Famciclovir is a prodrug that is converted to penciclovir in the body.

In view of the foregoing, there has been a long-felt but unmet need to find effective topical treatments for genital herpes and other herpetic lesions, such as oral herpes and shingles.

SUMMARY

It has now been found that a topical composition comprising dimethyl sulfoxide (DMSO), a quaternary ammonium compound (QAC) or other anti-viral agent, and a diluent, such as water and/or polyol, is effective in treating herpes lesions when topically applied to the affected area.

In embodiments, the herpes lesions are related to genital herpes, oral herpes, or shingles. Application of the topical composition to herpes lesions has been found to reduce the time of healing.

Moreover, application of the topical compositions disclosed herein can prophylactically prevent or reduce the number of outbreaks normally experienced by a person with a herpetic infection.

In embodiments, the compositions may further include other agents that can sooth pain and discomfort associated with herpes, such as a cannabinoid (e.g., cannabidiol (CBD) and/or tetrahydrocannabinol (THC)).

Anti-viral agents that can be used instead of or in addition to the QAC include acyclovir, val acyclovir, famciclovir, and penciclovir.

Amino acids, such as lysine or salt thereof, have been found to enhance effectiveness of the topical composition.

Camphor, essential oils and/or one or more terpenes can be added to provide a soothing effect.

It is to be understood that both the foregoing general description and the following detailed description are exemplary and explanatory only and are not restrictive of the embodiments claimed.

DETAILED DESCRIPTION OF THE PREFERRED EMBODIMENTS

Examples

Example 1

A topical treatment composition for treating genital herpes was made by combining the following components:

| | |
|---|---|
| Liquid Carrier | 99.87% (w/w) |
| Dimethyl sulfoxide (DMSO) | 70% (v/v) of carrier |
| Distilled Water | 30% (v/v) of carrier |
| Benzalkonium chloride | 0.13% (w/w) |

The treatment composition was a clear colorless liquid.

A person suffering from genital herpes applied the composition to the genital region during an outbreak. The person re-applied the composition once each day thereafter until the outbreak ceased. The outbreak was shortened by 3-5 days compared to the usual outbreak.

The person continued applying the composition to the affected area and went about 8 months without having a breakout, which normally occurred every few weeks unless an oral anti-viral composition (acyclovir) was taken. This was an unexpected and unpredictable result. It also shows the composition was effective as a prophylactic treatment to reduce, reduce or delay a breakout of lesions.

Example 2

The treatment composition of Example 1 was modified by adding an amount of CBD oil to yield a composition having 0.25% of cannabidiol (CBD). The composition had the same outbreak shortening effect as in Example 1 but with reduced pain and inflammation.

Example 3

The treatment composition of Example 1 was modified by adding an amount of lysine HCl to yield a composition containing 3% w/v of lysine HCl. The composition appeared to have the same or better outbreak shortening effect as in Example 1.

Example 4

A topical treatment composition for treating genital herpes is made by combining the following components:

| | |
|---|---|
| Liquid Carrier | 99.50% (w/w) |
| Dimethyl sulfoxide (DMSO) | 70% (v/v) of carrier |
| Distilled Water | 30% (v/v) of carrier |
| Benzalkonium chloride | 0.13% (w/w) |
| Cannabidiol (CBD) | 0.37% (w/w) |

The treatment composition is a yellow tinted tincture and was found to be effective in treating genital herpes similar to the compositions of Examples 1 and 2.

Example 5

A two-component topical treatment system for treating genital herpes is made that includes a first treatment composition for initial application and a second treatment composition or subsequent application.

| First Treatment Composition | |
|---|---|
| Liquid Carrier | 99.87% (w/w) |
| Dimethyl sulfoxide (DMSO) | 70% (v/v) of carrier |
| Distilled Water | 30% (v/v) of carrier |
| Benzalkonium chloride | 0.13% (w/w) |

| Second Treatment Composition | |
|---|---|
| Liquid Carrier | 99.75% (w/w) |
| Dimethyl sulfoxide (DMSO) | 70% (v/v) of carrier |
| Distilled Water | 30% (v/v) of carrier |
| Cannabidiol (CBD) | 0.25% (w/w) |

The first treatment composition was applied by a subject when at the initial phase of an outbreak, including one application the first day and then re-applied one or more times during the outbreak.

The second treatment composition was applied for 1-3 days after applying the first treatment composition to reduce inflammation and pain.

Example 6

A commercially available CBD hand and body lotion (CBD SFV/Klashnikova Migraine & Pain Terpenes) sold by Koodegras (Sandy, Utah), which contained 400 mg CBD in 6 fluid ounces of lotion, was mixed with DMSO, glycerin, and benzalkonium chloride to form a topical composition in the following amounts:

| | |
|---|---|
| CBD Lotion | 40 grams |
| DMSO | 30 milliliters |
| Glycerin | 10 milliliters |
| Benzalkonium chloride | 0.13% by weight of composition |

The CBD lotion contained the following: capric/caprillic triglycerides, sunflower seed oil, hemp CBD oil with terpenes, Moroccan organic argan oil, emulsifying wax, glyceryl monostearate, simmondsia (jojoba) oil, butyrospermum parkii (shea butter), stearic acid, cetyl alcohol, glyceryl distearate, and carbomer.

The resulting topical composition was a thin cream that remained as a stable emulsion.

A man suffering from genital herpes applied the composition to the genital region directly on the lesions and surrounding tissue and massaged it in gently. The composition was re-applied each day until the outbreak ceased. The lesions healed 3-5 days sooner than during the usual outbreak.

A woman suffering from genital herpes applies the composition to the genital region directly on the lesions and surrounding tissue and massages it in gently. The composition is re-applied each day until the outbreak ceases. The lesions heal 3-5 days sooner than during the usual outbreak.

Example 7

A commercially available CBD black seed salve (Sacred Herbal Medicinal Remedies) sold by Koodegras, which contained 900 mg CBD in 6 fluid ounces of salve, was with DMSO, glycerin, and benzalkonium chloride to form a topical composition in the following amounts:

| | |
|---|---|
| CBD Salve | 40 grams |
| DMSO | 30 milliliters |
| Glycerin | 10 milliliters |
| Benzalkonium chloride | 0.13% by weight of composition |

The CBD salve contained the following: organic olive oil, black seed (cumin) oil, coconut oil, jojoba oil, sweet almond oil, argan oil, nigella sativa oil, shea butter, beeswax, hemp CBD oil, skullcap charcoal, arnica, passionflower, Vitamin E, tocopherol, camphor, white willow oil, rosemary, turmeric lavender, frankincense, capsicum annum, and essential oils and herbal blends (proprietary).

The resulting topical composition was a thick emulsion that appeared to be relatively stable overnight.

A man suffering from genital herpes applies the composition to the genital region directly on the lesions and surrounding tissue and massages it in gently. The composition is re-applied each day until the outbreak ceases. The lesions heal 3-5 days sooner than during the usual outbreak.

A woman suffering from genital herpes applies the composition to the genital region directly on the lesions and surrounding tissue and massages it in gently. The composition is re-applied each day until the outbreak ceases. The lesions heal 3-5 days sooner than during the usual outbreak.

Example 8

A commercially available CBD salve (No. 9 Time-Released Quick Relief Salve) sold by Koodegras, which contained 200 mg CBD in 2 fluid ounces of salve, is mixed with a liquid carrier comprising DMSO (70%) and vegetable glycerin (30%) at a ratio of 1:1 to form a topical composition. An amount of benzalkonium chloride is added to achieve a concentration of 0.13% by weight of the composition.

The CBD salve contained the following: argan oil, black seed oil, olive oil, organic beeswax, proprietary Asian herbal mix, Vitamin E oil, mixed tocopherols, anhydrous hemp oil, time release CBD oil, proprietary essential oil blend, *melaleuca* oil, *eucalyptus* oil, cayenne oil, and beta-caryophyllene.

The resulting topical composition is a thick emulsion that is relatively stable but may require occasional agitation to resuspend. Addition of vegetable glycerin may help stabilize the composition and reduce odor of the DMSO.

A person suffering from genital herpes applies the composition to the genital region directly on the lesions and surrounding tissue and massages it in gently. The composition is re-applied each day until the outbreak ceases. The lesions heal 3-5 days sooner than during the usual outbreak.

Example 9

A commercially available CBD and THC infused balm (Energy Relief) sold by Planet 13, which contains 50 mg THC and 50 mg CBD in 50 grams of balm, is mixed with a liquid carrier comprising DMSO (70%) and vegetable glycerin (30%) at a ratio of 1:1 to form a topical composition. An amount of benzalkonium chloride is added to achieve a concentration of 0.13% by weight of the composition.

The CBD and THC infused balm contained the following: olive oil (extra virgin), lobelia olive oil, beeswax, castor oil, CBD isolate, cocoa butter, essential oil blend (proprietary), and THC. Total cannabinoid analysis in 100 mg of cannabinoids: 45.939 mg THC, 49.824 mg CBD, 0.0 mg CBG, 4.191 mg THCV, and 0.0 mg THCVa. Total terpenes: eucalyptol 13.546, camphene 9.220 mg, alpha-pinene 24.648 mg, and linalool 11.024 mg.

The resulting topical composition is a thin runny suspension that appears to be a relatively stable emulsion but may need agitation before use. The vegetable glycerin helps stabilize the composition and reduce odor of the DMSO.

A person suffering from genital herpes applies the composition to the genital region directly on the lesions and surrounding tissue and massages it in gently. The composition is re-applied each day until the outbreak ceases. The lesions heal 3-5 days sooner than during the usual outbreak.

Example 10

A commercially available water-borne nanosized CBD dispersion (Angstrom PlexII phytocannabinoid complex) sold by Koodegras, which contained 250 mg CBD in 10 milliliters, is mixed with mixed with a liquid carrier comprising DMSO (70%) and vegetable glycerin (30%) at a ratio of 1:1 to form a topical composition. An amount of benzalkonium chloride is added to achieve a concentration of 0.13% by weight of the composition.

The CBD suspension contained the following: purified water, olive oil, sunflower lecithin, anhydrous hemp oil, potassium sorbate, Vitamin E, and citric acid.

The resulting topical composition is a thin non-viscous fluid suspension that is relatively stable but may require occasional agitation to resuspend. Addition of vegetable glycerin may help stabilize the suspension and reduce odor of the DMSO.

A person suffering from genital herpes applies the composition to the genital region directly on the lesions and surrounding tissue and massages it in gently. The composition is re-applied each day until the outbreak ceases. The lesions heal 3-5 days sooner than during the usual outbreak.

Example 11

Any of the topical compositions of Examples 1-10 is modified by adding camphor, such as in a range of about 0.05% to about 1%, or about 0.075 to about 0.5%, or about 0.1% w/v.

Example 12

Any of the topical compositions of Examples 1-11 is modified by adding a therapeutically effective amount of an anti-viral compound selected from acyclovir, valacyclovir, famciclovir, or penciclovir, optionally to replace at least some of the benzalkonium chloride.

Example 13

A kit is made that contains any of the topical compositions of Examples 1-12 packaged together with an oral dosage form of lysine, such as lysine HCl. The oral dosage form is a tablet, capsule or liquid and provides from 1-3 g/day of lysine.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treating a herpes infection comprising topically applying a topical treatment composition to a treatment site of a person in need thereof, the topical treatment composition comprising:
   a liquid carrier comprising dimethyl sulfoxide (DMSO) and a diluent; and
   an anti-viral agent comprising at least one water soluble quaternary ammonium compound included at a concentration so that, when applied to the treatment site together with the DMSO, treats the herpes infection by providing anti-viral activity at the treatment site, wherein the liquid carrier comprises 50-70% DMSO and 50-30% diluent and the at least one water soluble quaternary ammonium compound comprises benzalkonium chloride.

2. The method of claim 1, wherein the diluent comprises water.

3. The method of claim 1, wherein the diluent comprises one or more polyols selected from glycerin, propylene glycol, 1,3-propanediol, 1,3-butanediol, sorbitol, xylitol, and polyethylene glycol.

4. The method of claim 1, the topical treatment composition further comprising a cannabinoid component selected from cannabidiol (CBD), tetrahydrocannabinol (THC), cannabinol (CBN), cannabigerol (CBG), cannabichchromene (CBC), cannabicyclol (CBL), tetrahydrocannabivarin (THCV), cannabidivarin (CBDV), cannabichromevarin (CBCV), cannabigerovarin (CBGV), delta-8-tetrahydrocannabinol, delta-9-tetrahydrocannabinol (Dronabinol), cannabigerol monomethyl ether (CBGM), and nabilone.

5. The method of claim 4, wherein the cannabinoid component is water insoluble and in the form of liposomal droplets, aqueous nanosized cannabinoid dispersion, water-in-oil emulsion, or oil-in-water emulsion.

6. The method of claim 1, the topical treatment composition further comprising at least one fatty component, including one or more fatty components selected from fatty acids, such as capric acid, caprillic acid, lauric acid, medium chain fatty acid (8 to 10 carbons), stearic acid, isostearic acid, octanoic acid, oleic acid, linoleic acid, or linolenic acid, esters of fatty acids, such as mono-, di- and/or triglycerides of fatty acids, preferably one or more of olive oil, sunflower seed oil, coconut oil, cocoa butter, jojoba oil, almond oil, pine needle oil, shea butter, argan oil, nigella sativa oil, beeswax, and flaxseed oil, wherein the topical treatment composition is an emulsion.

7. The method of claim 1, wherein the composition is a cream, lotion, gel, suspension, ointment, high-viscosity liquid, medium viscosity liquid, or low viscosity liquid.

8. The method of claim 1, the topical treatment composition further comprising at least one terpene or essential oil.

9. The method of claim 1, the topical treatment composition further comprising lysine or salt thereof.

10. The method of claim 1, the topical treatment composition further comprising an additional anti-viral agent selected from the group consisting of acyclovir, valacyclovir, famciclovir, and penciclovir.

11. The method of claim 1, wherein the treatment site is a region that has or is prone to an outbreak of one or more herpetic lesions.

12. The method of claim 1, wherein the herpes infection is genital herpes.

13. The method of claim 1, wherein the herpes infection is oral herpes.

14. The method of claim 1, wherein the herpes infection is shingles.

15. A method of treating a herpes infection comprising topically applying first and second topical treatment compositions to a treatment site of a person in need thereof, the first topical treatment component comprising:
a liquid carrier comprising dimethyl sulfoxide DMSO and a diluent, wherein the diluent comprising at least one of water or polyol; and
an anti-viral component comprising a water soluble quaternary ammonium compound included in a concentration so that, when applied to the treatment site together with the DMSO, treats the herpes infection by providing anti-viral activity at the treatment site,
wherein the liquid carrier comprises 50-70% DMSO and 50-30% diluent and the at least one water soluble quaternary ammonium compound comprises benzalkonium chloride; and
the second topical treatment component comprising:
a liquid carrier comprising dimethyl sulfoxide DMSO and a diluent; and
at least one of a cannabinoid or lysine.

16. The method of claim 15, wherein the anti-viral component further includes another anti-viral selected from the group consisting of acyclovir, valacyclovir, famciclovir, and penciclovir.

17. A method of treating a herpes infection comprising applying a topical component of a two-component composition to a treatment site of a person in need thereof and orally administering an oral dosage form of the two-component composition to person, the topical component comprising:
a liquid carrier comprising dimethyl sulfoxide DMSO and an aqueous diluent; and
an anti-viral component that is water soluble and comprises one or more of a quaternary ammonium compound, acyclovir, valacyclovir, famciclovir, or penciclovir in a concentration so that, when applied to the treatment site together with the DMSO, treats the herpes infection by providing anti-viral activity at the treatment site,
wherein the liquid carrier comprises 50-70% DMSO and 50-30% diluent and the at least one water soluble quaternary ammonium compound comprises benzalkonium chloride; and
the oral dosage form comprising lysine.

18. The method of claim 1, wherein the DMSO is included at a concentration of about 70% by volume of the liquid carrier and the benzalkonium chloride is included at a concentration of about 0.13% by weight of the topical treatment composition.

19. The method of claim 15, wherein the benzalkonium chloride is included at a concentration of about 0.13% by weight of the first topical treatment composition.

\* \* \* \* \*